(12) United States Patent
Magnuson

(10) Patent No.: US 6,452,073 B1
(45) Date of Patent: Sep. 17, 2002

(54) GARDEN BEAN NAMED 208996

(75) Inventor: D. Stephen Magnuson, Gilroy, CA (US)

(73) Assignee: Harris Moran Seed Company, Modesto, CA (US)

( * ) Notice: Subject to any disclaimer, the term of this patent is extended or adjusted under 35 U.S.C. 154(b) by 0 days.

(21) Appl. No.: 09/726,126

(22) Filed: Nov. 30, 2000

(51) Int. Cl.⁷ .............................. A01H 5/00; A01H 5/10; A01H 1/00; C12N 15/82; C12N 5/04

(52) U.S. Cl. .................. 800/313; 800/266; 800/298; 800/300; 800/301; 800/278; 800/302; 800/267; 800/268; 435/410; 435/430; 435/421; 435/430.1

(58) Field of Search .................. 800/300, 313, 800/301, 302, 260, 278, 266, 298, 268, 267; 435/410, 421, 420, 430.1, 430

(56) References Cited

U.S. PATENT DOCUMENTS 6,211,444 B1 * 4/2001 Gehin

OTHER PUBLICATIONS

R.W. Allard, Backcross Breeding, Copyright 1960, Principles of Plant Breeding, Library of Congress Catalog Card No.: 60–14240, pp. 155–156.*

* cited by examiner

Primary Examiner—David T. Fox
Assistant Examiner—David H Kruse
(74) Attorney, Agent, or Firm—Rothwell, Figg, Ernst & Figg

(57) ABSTRACT

A novel garden bean cultivar, designated 208996, is disclosed. The invention relates to the seeds of garden bean cultivar 208996, to the plants of garden bean 208996 and to methods for producing a garden bean plant produced by crossing the cultivar 208996 with itself or another garden bean variety. The invention further relates to hybrid garden bean seeds and plants produced by crossing the cultivar 208996 with another garden bean cultivar.

26 Claims, No Drawings

GARDEN BEAN NAMED 208996

BACKGROUND OF THE INVENTION

The present invention relates to a new and distinctive garden bean (*Phaseolus vulgaris* L.) variety, designated 208996. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm. These important traits may include fresh pod yield, higher seed yield, resistance to diseases and insects, better stems and roots, tolerance to drought and heat, and better agronomic quality. With mechanical harvesting of many crop, uniformity of plants characteristics such as germination and stand establishment, growth rate, maturity and plant height is important.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those elite in traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior garden bean cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line with the same garden bean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new garden bean cultivars.

The development of new garden bean cultivars requires the development and selection of garden bean varieties, the crossing of these varieties and selection of superior hybrid crosses. The hybrid seed is produced by manual crosses between selected parents. These hybrids are selected for certain genetic traits such as pod straightness, erect habit, root structure and disease resistance.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Garden bean, *Phaseolus vulgaris* L., is an important and valuable vegetable crop. Thus, a continuing goal of plant breeders is to develop stable, high yielding garden bean cultivars that are agronomically sound. The reasons for this goal are obviously to maximize the amount of yield produced on the land. To accomplish this goal, the garden bean breeder must select and develop garden bean plants that have the traits that result in superior cultivars.

SUMMARY OF THE INVENTION

According to the invention, there is provided a novel garden bean cultivar, designated 208996. This invention thus relates to the seeds of garden bean cultivar 208996, to the plants of garden bean 208996 and to methods for producing a garden bean plant produced by crossing the garden bean 208996 with itself or another garden bean line.

Thus, any such methods using the garden bean variety 208996 are part of this invention: selfing, backcrosses, hybrid production, crosses to populations, and the like. All plants produced using garden bean variety 208996 as a parent are within the scope of this invention. Advantageously, the garden bean variety could be used in crosses with other, different, garden bean plants to produce first generation ($F_1$) garden bean hybrid seeds and plants with superior characteristics.

Parts of the garden bean of the present invention such as ovule and pollen are also provided.

In another aspect, the present invention provides regenerable cells for use in tissue culture of garden bean plant 208996. The tissue culture will preferably be capable of regenerating plants having the physiological and morphological characteristics of the foregoing garden bean plant, and of regenerating plants having substantially the same genotype as the foregoing garden bean plant. Preferably, the regenerable cells in such tissue cultures will be embryos, protoplasts, seeds, callus, pollen, leaves, anthers, roots, and meristematic cells. Still further, the present invention provides garden bean plants regenerated from the tissue cultures of the invention.

In another aspect, the present invention provides for single gene converted plants of 208996. The single transferred gene may preferably be a dominant or recessive allele. Preferably, the single transferred gene will confer such trait as herbicide resistance, insect resistance, resistance for bacterial, fungal, or viral disease, enhanced nutritional quality, and industrial usage. The single gene may be a naturally occurring bean gene or a transgene introduced through genetic engineering techniques.

The invention further provides methods for developing bean plants in a bean plant breeding program using plant breeding technique including recurrent selection, backcrossing, pedigree breeding, restriction fragment length polymorphism enhanced selection, genetic marker enhanced selection and transformation. Seeds, bean plant, and parts thereof produced by such breeding methods are also part of the invention.

Definitions

In the description and tables which follow, a number of terms are used. In order to provide a clear and consistent understanding of the specification and claims, including the scope to be given such terms, the following definitions are provided:

Maturity Date. Plants are considered mature when the pods have reached their maximum allowable seed size and sieve size for the specific use intended. This can vary for each end user, e.g., processing at different stages of maturity would be required for different types of consumer beans such as "whole pack," "cut" or "french style". The number of days are calculated from a relative planting date which depends on day length, heat units and environmental other factors.

Sieve Size (sv). Sieve size 1 means pods which fall through a sieve grader which culls out pod diameters of 4.76 cm through 5.76 cm. Sieve size 2 means pods which fall through a sieve grader which culls out pod diameters of 5.76 cm through 7.34 cm. Sieve size 3 means pods which fall through a sieve grader which culls out pod diameters of 7.34 cm through 8.34 cm. Sieve size 4 means pods which fall through a sieve grader which culls out pod diameters of 8.34 cm through 9.53 cm. Sieve size 5 means pods which fall through a sieve grader which culls out pod diameters of 9.53 cm through 10.72 cm. Sieve size 6 means pods which fall through a sieve grader which culls out pod diameters of 10.72 cm or larger.

Bean Yield (Tons/Acre). The yield in tons/acre is the actual yield of the bean pods at harvest.

Plant Height. Plant height is taken from the top of soil to top node of the plant and is measured in centimeters.

Allele. Allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

DETAILED DESCRIPTION OF THE INVENTION

Garden bean cultivar 208996 has superior characteristics and was developed from the cross M9227 (female) and M9079 (male), which was made in the fall of 1994 in the greenhouse at Harris Moran Research in California. The $F_1$ hybrids were grown in a greenhouse during the Spring of 1995. $F_2$ selection, plot number 1Y1007, was made at Heath Farm, Coloma, Wis. in the Summer of 1995. The $F_3$ selections were made in the Fall of 1995 at San Juan Bautista, Calif. $F_4$ plants were selected in a field plot in California in September 1996; $F_5$ selections were made in the Summer of 1997 in Heath Farm, Coloma, Wis.; $F_6$ generation was bulked in field plots near Los Mochis, Sinaloa, Mexico in February, 1998 for observation at selected location in summer 1998. $F_7$ plants were selected in a field plot at San Juan Bautista, Calif. in Summer 1998 from the previous bulked plants. $F_8$ plants were selected and bulked in field plots near Los Mochis, Sinaloa, Mexico in February, 1999. The $F_9$ generation is a stock seed increase at San Juan Bautista, Calif.

208996 is a green snapbean with attractive, dark, glossy pods and rust resistance to three key races of rust that gives 208996 a superior advantage domestically but also internationally where rust disease is a limiting factor. In trials in the United States, Japan and South Africa, 208996 has shown excellent fresh pod yielding ability and plant adaptability.

Some of the criteria used to select in various generations include: pod appearance and length, fresh pod yield, pod set height, emergence, maturity, plant architecture, seed yield and quality, and disease resistance, especially rust resistance.

Rust resistance is an especially desired trait for a new bean variety. Indeed, the bean rust pathogen *Uromyces appendiculatus* may cause yield losses which can approach 100% and that are related to earliness and severity of infection. The disease occurs worldwide. Bean rust most frequently affects leaves but also affects pods, stem, and all other above ground, green portions of bean plants. The common sign of bean rust is the reddish brown, circular uredinial pustule on leaves or pods which ruptures the epidermis to produce abundant, powdery urediniospores. Larger uredinia are often surrounded by a halo of yellow host tissue and may be surrounded by a ring of smaller secondary uredinia (Compendium of Bean Diseases, 1991. Edited by Robert Hall. APS Press). Some bean are resistant to a few races of the rust pathogen, but only a few are resistant to the most infectious ones. 208996, being resistant to races 38, 53 and 72 can face a broad range of worldwide infections. Resistance reactions are graded as immune (no symptoms) non sporuling necrotic spots, ranging from less than 0.3 to 5 or more mm in diameter and very small, small or moderate uredinia. 208996 is immune to races 38 and 72 and clearly demonstrate a very good resistance to race 53, this resistance being characterized by pustules having a diameter less than 3 microns, not likely observable in field condition and causing no observable harm to the plant.

The cultivar has shown uniformity and stability, as described in the following variety description information. It has been self-pollinated a sufficient number of generations with careful attention to uniformity of plant type. The line has been increased with continued observation for uniformity.

Garden bean cultivar 208996 has the following morphologic and other characteristics (based on data collected at San Juan Bautista).

VARIETY DESCRIPTION INFORMATION

1. Market Maturity
   Days to edible pods: 72 days
   Number of days earlier than 'Paulista': 0 days
2. Plant
   Habit: determinate
   Height: 36 cm
   Taller than 'Paulista' by 6 cm
   Spread: 31 cm
   Narrower than 'Paulista' by 3 cm
   Plant Shape: High bush form
3. Leaves
   Surface: intermediate
   Size: medium
   Color: dark green
4. Anthocyanin Pigment
   Flowers: Absent
   Stems: Absent
   Pods: Absent
   Seeds: Absent
   Leaves: Absent
   Petioles: Absent
   Peduncles: Absent
   Nodes: Absent
5. Flower Color
   Color of standard: white
   Color of wings: white
   Color of keel: white
6. Pods (Edible Maturity)
   Exterior color: dark green, glossy (shiny)
   Processed pods: dark green
   Dry pod color: buckskin
   Pod shape: 2.5–[3=round; 4=figure eight]
   Creaseback: present
   Pubescence: none
   Constriction: none
   Spur length: 7 mm
   Fiber: none
   Number seeds/pod: 6
   Suture string: absent Seed development: slow Machine harvest: adapted Distribution of sieve size at optimum maturity:
- 3% 4.76–5.76 mm—Sieve 1
- 16% 5.76–7.34 mm—Sieve 2
- 53% 7.34–8.34 mm—Sieve 3
- 28% 8.34–9.53 mm—Sieve 4

Average Length of 3 sieve: 13.5 cm

Average Length of 4 sieve: 14.5 cm

7. Seed Color

Seed coat luster: semi-shiny

Seed coat: monochrome

Primary color: white

Hilar ring: absent

8. Seed Shape and Size

Hilum view: elliptical

Cross section: oval

Side view: oval to oblong

Seed size: 20.6 gm/100 seeds

Lighter than 'Labrador' by 6.5 gm/100 seeds

9. Disease Resistance

Bean Common Mosaic Virus (BCMV)—Resistant

Beet Curly Top Virus (BCTV) Resistant

Bean Rust (Uromyces appendiculatus)
- Races 38 immune
- Race 53 resistant
- Race 72 immune The cultivar 208996 has dark, glossy, attractive fresh market pods, with a high pod set height, which are on an erect machine harvestable bush. 208996 is resistant to Bean Common Mosaic Virus and Beet Curly Top Virus. 208996 is immune to rust races 38, and 72 and resistant to rust race 53. The frozen product of 208996 is attractive with a uniform dark pod color.

The cultivar 208996 is most similar to 'Paulista' but differs in that 208996 is resistant to rust races 38, 53 and 72 whereas 'Paulista' is susceptible. 208996 is also easily distinguished by a much darker pod than 'Paulista'.

TABLES

In Table 1 that follows, the percentage of bean pod with different sieve sizes is shown for year 1998. The first column lists the variety tested. The second shows the location. Columns 3–5 show the percentage of beans for different sieve sizes 2, 3 and 4 respectively. Column 6 lists the yield in tons per acre and column 7 has days to maturity.

TABLE 1

| Variety | Location | % 2 sv | % 3 sv | % 4 sv | Yield T/Acre | Days to Maturity |
| --- | --- | --- | --- | --- | --- | --- |
| 208996 | California | 16 | 53 | 28 | 2.4 | 72 |
| 'Paulista' | California | 14 | 61 | 24 | 2.0 | 72 |
| 'Xera' | California | 21 | 63 | 13 | 2.0 | 72 |

In Table 2 that follows, the yield in tons per acre is shown for year 1999. The first column lists the variety tested. The second shows the location and the third shows the yield. Column 4 shows the days to maturity, related to the location.

TABLE 2

| Variety | Location | Yield T/Acre | Days to Maturity |
| --- | --- | --- | --- |
| 208996 | Sun Prairie (Wisconsin) | 2.5 | 60 |
| 208996 | Sun Prairie (Wisconsin) | 3.4 | 60 |
| 208996 | Coloma (Wisconsin) | 4.2 | 60 |
| 'Paulista" | Coloma (Wisconsin) | 3.9 | 60 |

This invention is also directed to methods for producing a garden bean plant by crossing a first parent garden bean plant with a second parent garden bean plant, wherein the first or second garden bean plant is the garden bean plant from the line 208996. Further, both first and second parent garden bean plants may be from the cultivar 208996. Therefore, any methods using the cultivar 208996 are part of this invention: selfing, backcrosses, hybrid breeding, and crosses to populations. Any plants and seeds produced using cultivar 208996 as a parent are within the scope of this invention.

Still further, this invention is also directed to methods for producing a garden bean line 208996-derived bean plant by crossing bean line 208996 with a second bean plant and growing the progeny seed, and repeating the crossing and growing steps with the bean line 208996-derived garden plant from 0 to 7 times. The 208996-derived garden plant are also part of the invention.

As used herein, the term "plant" includes plant cells, plant protoplasts, plant cells of tissue culture from which garden bean plants can be regenerated, plant calli, plant clumps, and plant cells that are intact in plants or parts of plants, such as pollen, flowers, embryos, ovules, seeds, pods, leaves, stems, roots, anthers and the like.

The present invention contemplates a bean plant regenerated from a tissue culture of a variety (e.g. 208996) or a hybrid plant of the present invention. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, leaves, stems, roots, pods, anthers, and the like. In a preferred embodiment, tissue culture is embryos, protoplast, meristematic cells, pollen, leaves or anthers. Means for preparing and maintaining plant tissue culture are well known in the art.

As is well known in the art, tissue culture of garden bean can be used for the in vitro regeneration of a garden bean plant. Tissue culture of various tissues of garden beans and regeneration of plants therefrom is well known and widely published. For example, reference may be had to McClean, P.; Grafton, K. F. (1989): "Regeneration of dry bean (*Phaseolus vulgaris*) via organogenesis." *Plant Sci.* 60,117–122. Mergeai, G.; Baudoin, J. P. (1990): "Development of an in vitro culture method for heart-shaped embryo in *Phaseolus vulgarism*" B.I.C. Invit. Papers 33, 115–116. Vanderwesthuizen, A. J.; Groenewald, E. G. (1990): "Root Formation and Attempts to Establish Morphogenesis in Callus Tissues of Beans (*Phaseolus-Vulgaris* L.)." *S. Afr. J. Bot.* 56(2, April), 271–273. Benedicic, D., et al. (1990): "The regeneration of *Phaseolus vulgaris* L.plants from meristem culture." Abst. 5th I.A.P.T.C. Cong. 1, 91 (#A3-33). Genga, A.; Allavena, A. (1990): "Factors affecting morphogenesis from immature cotyledons of *Phaseolus coccineus* L." Abst. 5th I.A.P.T.C. Cong. 1, 101 (#A3-75). Vaquero, F., et al. (1990): "Plant regeneration and preliminary studies on transformation of *Phaseolus coccineus*." Abst. 5th I.A.P.T.C. Cong. 1, 106 (#A3-93). Franklin, C. I., et al. (1991): "Plant Regeneration from Seedling Explants of Green Bean (*Phaseolus-Vulgaris* L.) via Organogenesis." *Plant Cell Tissue Org. Cult.* 24(3, March), 199–206. Malik, K. A.; Saxena, P. K. (1991): "Regeneration in *Phaseolus-Vulgaris* L.—Promotive Role of N6-Benzylaminopurine in Cultures from Juvenile Leaves." *Planta* 184(1), 148–150. Genga, A.; Allavena, A. (1991): "Factors affecting morphogenesis from immature cotyledones of *Phaseolus coccineus* L." *Plant Cell Tissue Org. Cult.* 27, 189–196. Malik, K. A.; Saxena, P. K. (1992): "Regeneration in *Phaseolus vulgaris* L.L.— High-Frequency Induction of Direct Shoot Formation in Intact Seedlings by N-6-Benzylaminopurine and Thidiazuron." 186 (3, February), 384–389. Malik, K. A.; Saxena, P. K. (1992): "Somatic Embryogenesis and Shoot Regeneration from Intact Seedlings of *Phaseolus acutifolius* A., *P. aureus* (L.) Wilczek, *P. coccineus* L., and *P. wrightii* L." *Pl. Cell. Rep.* 11(3, April), 163–168. Chavez, J., et al. (1992): "Development of an in vitro culture method for heart shaped embryo in *Phaseolus polyanthus*." B.I.C. Invit. Papers 35, 215–216. Munoz-Florez, L. C., et al. (1992): "Finding out an efficient technique for inducing callus from Phaseolus microspores." B.I.C. Invit. Papers 35, 217–218. Vaquero, F., et al. (1993): "A Method for Long-Term Micropropagation of *Phaseolus coccineus* L." *L. Pl. Cell. Rep.* 12 (7–8, May), 395–398. Lewis, M. E.; Bliss, F. A. (1994): "Tumor Formation and beta-Glucuronidase Expression in *Phaseolus vulgaris* L.Inoculated with *Agrobacterium Tumefaciens*." *Journal of the American Society for Horticultural Science* 119 (2, March), 361–366. Song, J. Y., et al. (1995): "Effect of auxin on expression of the isopentenyl transferase gene (ipt) in transformed bean (*Phaseolus vulgaris* L.L.) single-cell clones induced by *Agrobacterium tumefaciens* C58." *J. Plant Physiol.* 146 (1–2, May), 148–154.

Thus, another aspect of this invention is to provide cells which upon growth and differentiation produce garden bean plants having the physiological and morphological characteristics of variety 208996.

The present invention encompasses methods for producing a bean plant containing in its genetic material one or more transgene and the transgenic bean plant produced by that method.

The molecular techniques allow to engineer the genome of plants by adding or modifying foreign or endogenous genes (referred here as transgenes) in such a manner that the traits of the plant can be modified in a specific way. Plant transformation involves the construction of an expression vector comprising one or more genes under control or operatively linked to a regulatory element (e.g. a promoter). Such vector can be used to provide transformed bean plants, using transformation methods as described hereafter to incorporate the gene or the genes into the genetic material of the bean plant.

To facilitate the identification of transformed plant cells, the vector of this invention may include plant selectable markers. Selectable markers and uses are well known in the art and include enzymes which provide for resistance to antibiotics such as gentamycin (Hayford et al., Plant Physiol. 86: 1216 (1988)), hygromycin (Vanden Elzen et al., Plant Mol. Biol., 5: 299 (1985)), kanamycin (Fraley et al., Proc. Natl. Acad. Sci. U.S.A., 80: 4803 (1983)), and the like. Similarly, enzymes providing for production of a compound identifiable by color change such as GUS, (beta.-glucuronidase Jefferson, R. A., Plant Mol. Biol. Rep. 5: 387 (1987)), or luciferase are useful. GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.)

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells."Tissue-specific" promoters initiate transcription only in certain tissues, such as a pollen-specific promoter from Zm13 (Guerrero et al., Mol. Gen. Genet.224: 161–168 (1993). "Inducible" promoter is under environmental control, such as the inducible promoter from a steroid hormone gene, the transcriptional activity of which is induced by a glucocorticosteroid hormone. Schena et al., Proc. Natl. Acad. Sci. U.S.A. 88: 0421 (1991). Tissue-specific and inducible promoters are "non-constitutive" promoters. A "constitutive" promoter is a promoter which is active under most environmental conditions such as the 35S promoter from CaMV (Odell et al., Nature 313: 810–812 (1985) or the promoters from such genes as rice actin (McElroy et al., Plant Cell 2: 163–171 (1990)).

These regulatory sequences will allow the expression of the transgenes in the transformed cells, in the transformed plants. The transgenes may code for proteins including plant selectable markers but also proteins adding a value trait to the crop such as agronomic, nutritional or therapeutic value or proteins conferring resistance to diseases and/or pathogens (e.g. bacterial, fungal, insect or herbicide resistance).

Several techniques, depending on the type of plant or plant cell to be transformed, are available for the introduction of the expression construct containing a DNA sequence encoding an protein of interest into the target plants. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89–119.

Methods of introducing expression vectors into plant tissue include the direct infection or co-cultivation of plant cells with *Agrobacterium tumefaciens,* Horsch et al., Science, 227:1229 (1985). Descriptions of Agrobacterium vectors systems and methods for Agrobacterium-mediated gene transfer provided by Gruber, et al., supra.

Procedures for garden bean transformation have been described by: McClean, P., et al. (1991): "Susceptibility of Dry Bean (*Phaseolus-Vulgaris* L.) to AgrobacterumInfection—Transformation of Cotyledonary and Hypocotyl Tissues." *Plant Cell Tissue Org. Cult.* 24(2, February), 131–138. Russell, D. R., et al. (1993): "Stable Transformation of *Phaseolus vulgaris* L.via Electric-Discharge Mediated Particle Acceleration." *Pl. Cell. Rep.* 12(3, January), 165–169. Franklin, C. I., et al. (1993): "Genetic Transformation of Green Bean Callus via Agrobacterium Mediated DNA Transfer." *Pl. Cell. Rep.* 12(2, January), 74–79. Aragao, F. J. L., et al. (1992): "Particle Bombardment-Mediated Transient Expression of a Brazil Nut Methionine-Rich Albumin in Bean (*Phaseolus vulgaris* L.L.)." *Plant Mol. Biol.* 20(2, October), 357–359. Aragao, F. J. L., et al. (1993): "Factors Influencing Transient Gene Expression in Bean (*Phaseolus vulgaris* L.L.) Using an Electrical Particle Acceleration Device." *Pl. Cell. Rep.* 12(9, July), 483–490. Francisco Aragao (1996): "Inheritance of foreign genes in transgenic bean (*Phaseolus vulgaris* L.L.) co-transformed via particle bombardment." *Theor. Appl. Genet.* 93: 142–150. Zhang, Z., et al. (1997): "Factors Affecting Agrobacterum-mediated Transformation of Common Bean." *J. Amer. Soc. Hort. Sci.* 122(3): 300–305. Kim, J.; Minamikawa, T. (1996): "Transformation and regeneration of French bean plants by the particle bombardment process." *Plant Science* 1 17: 131–138. Saker, M.; Kuhne, T. (1997/98): "Production of transgenic kidney bean shoots by electroporation of intact cells." *Biologia Plantarum* 40(4): 507–514.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device Agrobacterium-medicated transformation. Transformant plants obtained with the protoplasm of the invention are intended to be within the scope of this invention.

Following transformation of bean target tissues, expression of the above-described selectable marker genes allows for preferential selection of transformed cells, tissues and/or plants, using regeneration and selection methods now well known in the art.

The transgenic lines produced by the forgoing methods could then be crossed, with another (non-transformed or transformed) line, in order to produce a new bean plant.

When the terms bean plant, bean cultivar or bean line are used in the context of the present invention, this also includes any single gene conversions of that line. The term single gene converted plant as used herein refers to those bean plants which are developed by a plant breeding technique called backcrossing wherein essentially all of the desired morphological and physiological characteristics of a line are recovered in addition to the single gene transferred into the cultivar via the backcrossing technique. Backcrossing methods can be used with the present invention to improve or introduce a characteristic into the line. The term backcrossing as used herein refers to the repeated crossing of a hybrid progeny back to one of the parental bean plants for that line. The parental bean plant which contributes the gene for the desired characteristic is termed the nonrecurrent or donor parent. This terminology refers to the fact that the nonrecurrent parent is used one time in the backcross protocol and therefore does not recur. The donor parent may, or may not be transgenic. The parental bean plant to which the gene or genes from the nonrecurrent parent are transferred is known as the recurrent parent as it is used for several rounds in the backcrossing protocol (Poehiman & Sleper, 1994,; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a bean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent line is modified or substituted with the desired gene from the nonrecurrent parent, while retaining essentially all of the rest of the desired genetic, and therefore the desired physiological and morphological, constitution of the original cultivar. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196; 5,948,957 and 5,969,212, the disclosures of which are specifically hereby incorporated by reference.

DEPOSIT INFORMATION

A deposit of the Harris Moran Seed Company Garden Bean Named 208996 disclosed above an recited in the appended claims has been made with the American Type Culture Collection (ATCCC), 10801 University Boulevard, Manassas, Va. 20110. The date of deposit was Jun. 14, 2002. The deposit of 2,500 seeds were taken from the same deposit maintained by Harris Moran Seed Company since prior to the filing date of this application. All restrictions upon the deposit have been removed, and the deposit is intended to meet all of the requirements of 37 C.F.R. §1.801–1.809. The ATCC accession number is PTA-4458. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A *Phaseolus vulgaris* L. garden bean seed designated 208996, wherein a sample of said seed has been deposited under ATCC Accession No. PTA-4458.

2. A plant, or its parts, produced by growing the seed of claim 1.

3. Pollen of the plant of claim 2.

4. An ovule of the plant of claim 2.

5. A *Phaseolus vulgaris* L. garden bean plant having all of the physiological and morphological characteristics of the garden bean plant of claim 2, or its parts.

6. A tissue culture of regenerable cells of a bean plant of variety 208996, wherein the cells regenerate plants expressing all the morphological and physiological characteristics of *Phaseolus vulgaris* L. bean line 208996, representative seeds having been deposited under ATCC number PTA-4458.

7. The tissue culture of claim 6, selected from the group consisting of protoplast and calli, wherein the regenerable cells are derived from embryo, meristematic cells, leaves, pollen, embryo, root, root tips, stems, anther, flowers, seeds or pods.

8. A *Phaseolus vulgaris* L. garden bean plant regenerated from the cells of claim 6, expressing all the morphological and physiological characteristics of *Phaseolus vulgaris* L. bean plant 208996, representative seeds having been deposited under ATCC number PTA-4458.

9. A method for producing a garden bean seed comprising crossing a first parent garden bean plant with a second parent garden bean plant and harvesting the resultant hybrid garden bean seed, wherein said first or second parent garden bean plant is the *Phaseolus vulgaris* L. garden bean plant of claim 2.

10. A hybrid garden bean seed produced by the method of claim 9.

11. A hybrid garden bean plant, or its parts, produced by growing said hybrid garden bean seed of claim 10.

12. A garden bean seed produced by growing said hybrid garden bean plant of claim 11 and harvesting the resultant bean seed.

13. A method for producing a hybrid bean seed comprising crossing a *Phaseolus vulgaris* L. bean plant according to claim 2 with another, different bean plant; and harvesting the resultant hybrid garden bean seed.

14. A hybrid bean seed produced by the method of claim 13.

15. A hybrid bean plant, or its parts, produced by growing said hybrid bean seed of claim 14.

16. A bean seed produced by growing said hybrid bean plant of claim 15 and harvesting the resultant seed.

17. A method for producing a 208996-derived bean plant, comprising:
   a) crossing bean line 208996, a sample of seed of said line having been deposited under ATCC accession number, with a second bean plant to yield progeny bean seed; and
   b) growing said progeny bean seed, under plant growth conditions, to yield said 208996-derived bean plant.

18. The method of claim 17, further comprising:
   c) crossing said 208996-derived bean plant with itself or another bean plant to yield additional 208996-derived progeny bean seed;
   d) growing said progeny bean seed of step (c) under plant growth conditions, to yield 208996-derived bean plant;
   e) repeating the crossing and growing steps of (c) and (d) from 0 to 3 times to generate a further 208996-derived bean plant.

19. The *Phaseolus vulgaris* L. bean plant, or parts thereof, of claim 2, wherein the plant or parts thereof have been transformed so that its genetic material contains one or more transgenes operably linked to one or more regulatory elements.

20. A method for producing a bean plant that contains in its genetic material one or more transgenes, comprising crossing the *Phaseolus vulgaris* L. bean plant of claim 19 with either a second plant of another bean line, or a non-transformed bean plant of the line 208996, so that the genetic material of the progeny that result from the cross contains the transgene(s) operably linked to a regulatory element.

21. A bean plant, or parts thereof, produced by the method of claim 20.

22. A method for developing a bean plant in a bean plant breeding program using plant breeding techniques which include employing a bean plant, or its parts, as a source of plant breeding material comprising: obtaining the *Phaseolus vulgaris* L. bean plant, or its parts, of claim 2 as a source of said breeding material.

23. The method of claim 22 wherein the plant breeding techniques are selected from the group consisting of: recurrent selection, backcrossing, pedigree breeding, restriction fragment length polymorphism enhanced selection, genetic marker enhanced selection, and transformation.

24. The *Phaseolus vulgaris* L. bean plant of claim 5, further comprising a single gene conversion.

25. The single gene conversion *Phaseolus vulgaris* L. bean plant of claim 24, where the gene is selected from the group consisting of: a transgenic gene, a dominant allele, and a recessive allele.

26. The single gene conversion *Phaseolus vulgaris* L. bean plant of claim 24, where the gene confers a characteristic selected from the group consisting of: herbicide resistance, insect resistance, resistance to bacterial disease, resistance to fungal disease, resistance to viral disease, and improved nutritional quality.

* * * * *